US012636320B2

(12) United States Patent
Moradian et al.

(10) Patent No.: US 12,636,320 B2
(45) Date of Patent: May 26, 2026

(54) METHODS AND AGENTS FOR TREATING SOLID TUMOR CANCERS

(71) Applicant: Salspera, LLC, Oakdale, MN (US)

(72) Inventors: Aydin S. Moradian, Sunfish Lake, MN (US); Daniel A. Saltzman, Mendota Heights, MN (US)

(73) Assignee: Salspera, LLC, Oakdale, MN (US)

( * ) Notice: Subject to any disclaimer, the term of this patent is extended or adjusted under 35 U.S.C. 154(b) by 746 days.

(21) Appl. No.: 17/788,915

(22) PCT Filed: Dec. 26, 2020

(86) PCT No.: PCT/US2020/067067

§ 371 (c)(1),
(2) Date: Jun. 24, 2022

(87) PCT Pub. No.: WO2021/134043

PCT Pub. Date: Jul. 1, 2021

(65) Prior Publication Data

US 2023/0057396 A1 Feb. 23, 2023

Related U.S. Application Data

(60) Provisional application No. 62/953,792, filed on Dec. 26, 2019.

(51) Int. Cl.
*A61K 35/74* (2015.01)
*A61K 9/00* (2006.01)
(Continued)

(52) U.S. Cl.
CPC ............ *A61K 35/74* (2013.01); *A61K 9/0053* (2013.01); *A61K 31/4745* (2013.01);
(Continued)

(58) Field of Classification Search
CPC .. A61K 35/74; A61K 9/0053; A61K 31/4745; A61K 31/519; A61K 31/7068;
(Continued)

(56) References Cited

U.S. PATENT DOCUMENTS 6,685,935 B1 2/2004 Pawelek et al.
7,588,767 B2 9/2009 Szalay et al.
(Continued)

FOREIGN PATENT DOCUMENTS

EP 833660 B1 12/2006
EP 2028270 A2 2/2009
(Continued)

OTHER PUBLICATIONS

Wasiluk et al. "QS310. Attenuated *Salmonella typhimurium* Expressing Human Interleukin-2 (IL-2) Invades Human Pancreatic Cancer Cells", Journal of Surgical Research, Feb. 2008, pp. 1-8, vol. 144 Issue 2.
(Continued)

*Primary Examiner* — Robert B Mondesi
(74) *Attorney, Agent, or Firm* — Fredrikson & Byron, P.A.

(57) ABSTRACT

The present disclosure provides a method of treating a solid tumor cancer. The method includes administering a combination to a subject in need thereof. The combination includes at least two chemotherapy agents and a dose of a composition consisting essentially of attenuated *Salmonella typhimurium*. The present disclosure also provides an anti-tumor agent for use in a method of treating cancer. In such instances, the anti-tumor agent may include the combination.

3 Claims, 7 Drawing Sheets

Specification includes a Sequence Listing.

(51) Int. Cl.
| | |
|---|---|
| *A61K 31/4745* | (2006.01) |
| *A61K 31/519* | (2006.01) |
| *A61K 31/7068* | (2006.01) |
| *A61P 35/00* | (2006.01) |

(52) U.S. Cl.
CPC ........ *A61K 31/519* (2013.01); *A61K 31/7068* (2013.01); *A61P 35/00* (2018.01)

(58) Field of Classification Search
CPC ........ A61K 2039/522; A61K 2039/523; A61K 2039/542; A61K 2039/545; A61K 2039/55533; A61K 2039/57; A61K 2039/585; A61K 31/513; A61K 31/555; A61K 38/2013; A61K 39/39; A61K 45/06; A61K 2300/00; A61P 35/00; A61P 1/18; A61P 35/04; Y02A 50/30; C12N 15/74; C12N 1/20; C07K 14/55
USPC ...................................................... 424/93.4
See application file for complete search history.

(56) References Cited

U.S. PATENT DOCUMENTS

| | | | |
|---|---|---|---|
| 8,066,987 B2 | 11/2011 | Moore et al. | |
| 8,221,739 B2 | 7/2012 | Leonard et al. | |
| 8,647,618 B2 | 2/2014 | Leonard et al. | |
| 2005/0244375 A1 | 11/2005 | Leonard et al. | |
| 2006/0105423 A1 | 5/2006 | Rapp et al. | |
| 2007/0128301 A1 | 6/2007 | Saltzman et al. | |
| 2007/0243310 A1 | 10/2007 | Leonard et al. | |
| 2008/0107758 A1 | 5/2008 | Crutchfield | |
| 2010/0098665 A1 | 4/2010 | Leonard et al. | |
| 2013/0045525 A1* | 2/2013 | Leonard ................. | A61P 35/00 435/252.3 |
| 2013/0295054 A1* | 11/2013 | Huang ................... | C12N 15/70 435/320.1 |

FOREIGN PATENT DOCUMENTS

| | | | |
|---|---|---|---|
| WO | 0032211 A1 | 6/2000 | |
| WO | 0124637 A1 | 4/2001 | |
| WO | 0226819 A2 | 4/2002 | |
| WO | 03063593 A1 | 8/2003 | |
| WO | 03072789 A2 | 9/2003 | |
| WO | 2005116233 A1 | 12/2005 | |
| WO | 2007025333 A1 | 3/2007 | |
| WO | 2007039192 A2 | 4/2007 | |
| WO | 2016145974 A1 | 9/2016 | |
| WO | 2018106754 A1 | 6/2018 | |

OTHER PUBLICATIONS

Abdulamir et al., "The tumoricidal activity of *Salmonella* and its role in treating cancers", Cancer Therapy, vol. 8, No. 8, Feb. 14, 2013, pp. 10-23.

Aston et al., "A systemic investigation of the maximum tolerated dose of cytotoxic chemotherapy with and without supportive care in mice," BMC Cancer, vol. 17, No. 684, pp. 1-10.

Atta, "Some characteristics of nigella (*Nigella sativa* L.) seed cultivated in Egypt and its lipid profile," Food Chemistry, vol. 83, 2003, p. 63.

Barnett et al., "*Salmonella typhimurium* Invades and Decreases Tumor Burden in Neuroblastoma," Journal of Pediatric Surgery, vol. 40, No. 6, 2005, pp. 993-998.

Batist et al., "Orally Administered Multiple Dose Saltikva (*Salmonella*-IL2) in Conjunction with Folfirinox in a Patient with Stage IV Pancreatic Cancer: A Case Report," Clinical Oncology: Case Reports, vol. 3, Issue 3, Jun. 2, 2020, 4 pages.

Carrega et al., "Natural Killers Are Made Not Born: How to Exploit NK Cells in Lung Malignancies," Frontiers in Immunology, vol. 8, Article 277, Mar. 2017, 7 pages.

Conroy et al., "FOLFIRINOX versus Gemcitabine for Metastatic Pancreatic Cancer," The New England Journal of Medicine, vol. 364, No. 19, May 12, 2011, pp. 1817-1825.

Curtiss III et al., "*Salmonella typhimurium* Deletion Mutants Lacking Adenylate Cyclase and Cyclic AMP Receptor Protein Are Avirulent and Immunogenic," Infection and Immunity, vol. 55, No. 12, Dec. 1987, pp. 3035-3043.

Drees et al., "Soluble production of a biologically active single-chain antibody against murine PD-L1 in *Escherichia coli*," Protein Expression and Purification, vol. 94, Feb. 2014, pp. 60-66.

Drees et al., "Vasculature Disruption Enhances Bacterial Targeting of Autochthonous Tumors," Journal of Cancer, vol. 6, No. 9, 2015, pp. 843-848.

Drees et al., "Attenuated *Salmonella enterica Tyhimurium* Reduces Tumor Burden in an Autochthonous Breast Cancer Model," Anticancer Research: International Journal of Cancer Research and Treatment, vol. 35, 2015, pp. 843-850.

Eckenberg et al., "Analysis of Human IL-2/IL-2 Receptor B chain interactions: Monoclonal Antibody H2-8 and new IL-2 Mutants define the critical role of a Helix-A of IL-2," Cytokine, vol. 9, No. 7, 1997, pp. 488-498.

Feltis et al., "Cyclooxygenase 2 inhibition augments the hepatic antitumor effect of oral *Salmonella typhimurium* in a model of mouse metastatic colon cancer," Diseases of the Colon and Rectum, vol. 45, No. 8, Aug. 2002, pp. 1023-1028.

Feltis et al., "Liver and Circulating NK1.1+CD3—Cells Are Increased in Infection with Attenuated *Salmonella typhimurium* and Are Associated with Reduced Tumor in Murine Liver Cancer," Journal of Surgical Research, vol. 107, No. 1, Sep. 2002, pp. 101-107.

Flickinger Jr. et al., "Listeria monocytogenes as a Vector for Cancer Immunotherapy: Current Understanding and Progress," Vaccines, vol. 6, No. 3, 2018, 19 pages.

Forbes, "Engineering the perfect (bacterial) cancer therapy," Nature Reviews Cancer, Advance Online Publication, 2010, 10 pages.

Fritz et al., "A phase I clinical study to evaluate safety of orally administered, genetically engineered *Salmonella enterica* serovar *Typhimurium* for canine osteosarcoma," Veterinary Medicine and Science, vol. 2, No. 3, Jun. 6, 2016, pp. 179-190.

Galan et al., "Cloning and characterization of the asd gene of *Salmonella typhimurium*: use in stable maintenance of recombinant plasmids in *Salmonella* vaccine strains," Gene, vol. 94, 1990, pp. 29-35.

Gniadek et al., "A Phase I, Dose Escalation, Single Dose Trial of Oral Attenuated *Salmonella typhimurium* Containing Human IL-2 in Patients With Metastatic Gastrointestinal Cancers," Journal of Immunotherapy, vol. 43, No. 7, Sep. 2020, pp. 217-221.

Gulig et al., "Plasmid-Associated Virulence of *Salmonella typhimurium*," Infection and Immunity, vol. 55, No. 12, Dec. 1987, pp. 2891-2901.

International Patent Application No. PCT/US2020/067067, International Search Report & Written Opinion mailed May 26, 2021, 14 pages.

Kimchi-Sarfaty et al., "A "Silent" Polymorphism in the MDR1 Gene Changes Substrate Specificity" Science, vol. 315, Jan. 2007, pp. 525-528.

Lesterhuis et al., "Synergistic Effect of CTLA-4 Blockade and Cancer Chemotherapy in the Induction of Anti-Tumor Immunity," PLOS One, vol. 8, No. 4, Apr. 2013, pp. 1-8.

Mercado-Lubo et al., "A *Salmonella* nanoparticle mimic overcomes multidrug resistance in tumours," Nature Communications, vol. 7, No. 12225, Jul. 25, 2016, 13 pages.

Mi et al., "*Salmonella*-Mediated Cancer Therapy: An Innovative Therapeutic Strategy," Journal of Cancer, vol. 10, No. 20, Aug. 20, 2019, pp. 4765-4776.

Murakami et al., "Tumor-targeting Salmonella typhimurium A1-R in combination with doxorubicin eradicate soft issue sarcoma in a patient-derived orthotopic xenograft (PDOX) model," Oncotarget, vol. 7, No. 11, Mar. 15, 2016, pp. 12783-12790.

Nelson, "Antioxidant oil augments cytotoxic immune response to attenuated *Salmonella typhimurium*," Department of Surgery, University, XP-002460183, Apr. 30, 2003.

Noone et al., "SEER Cancer Statistics Review, 1975-2015," National Cancer Institute, 2018, 102 pages.

(56) References Cited

OTHER PUBLICATIONS

Owen et al., "The antioxidant/anticancer potential of phenolic compounds isolated from olive oil," European Journal of Cancer, vol. 36, 2000, pp. 1235-1247.

Parker et al., "Fatty Acid Composition and Oxidative Stability of Cold-pressed Edible Seed Oils," Journal of Food Science, vol. 68, No. 4, 2003, pp. 1240-1243.

Parry et al., "Fatty acid content and antioxidant properties of cold-pressed black raspberry seed oil and meal," Journal of Food Science, vol. 69, No. 3, 2004, pp. 189-193.

Saltzman et al. "Attenuated Salmonella typhimurium Containing Interleukin-2 Decreases MC-38 Hepatic Metastases: A Novel Anti-tumor Agent," Cancer Biotherapy and Radiopharmaceuticals, vol. 11, No. 2, 1996, pp. 145-153.

Saltzman et al., "Antitumor Mechanisms of Attenuated Salmonella typhimurium Containing the Gene for Human Interleukin-2: A Novel Antitumor Agent?" Journal of Pediatric Surgery, vol. 32, No. 2, Feb. 1997, pp. 301-306.

Saltzman et al., "Patterns of Hepatic and Splenic Colonization for the Attenuated Salmonella typhimurium Containing the Gene for Human Interleukin-2: A Novel Anti-Tumor Agent," Cancer Biotherapy & Radiopharmaceuticals, vol. 12, No. 1, Feb. 1997, pp. 37-45.

Saltzman, "Cancer immunotherapy based on the killing of Salmonella typhimurium-infected tumour cells," Expert Opinion on Biological Therapy, vol. 5, No. 4, 2005, pp. 443-449.

Saltzman et al., "Low dose chemotherapy combined with attenuated Salmonella decreases tumor burden and is less toxic than high dose chemotherapy in an autochthonous murine model of breast cancer," Surgery, vol. 163, No. 3, 2018, pp. 509-514.

Saltzman, "Project Stealth: Daniel Saltzman at TEDxCarletonCollege," TEDx Talks, published Nov. 30, 2013, Retrieved online from <https://www.youtube.com/watch?v=2gUBvjdlymE> on May 17, 2019, 2 pages.

Schodel et al., "Hybrid hepatitis B virus core-pre-S proteins synthesized in avirulent Salmonella typhimurium and Salmonella typhi for oral vaccination", Infect Immun., vol. 62, No. 5, May 1994, pp. 1669-1676.

Sorenson et al., "Attenuated Salmonella typhimurium with interleukin 2 gene prevents the establishment of pulmonary metastases in a model of osteosarcoma," Journal of Pediatric Surgery, vol. 43, 2008, pp. 1153-1158.

Sorenson et al., "Attenuated Salmonella typhimurium with IL-2 Gene Reduces Pulmonary Metastases in Murine Osteosarcoma," Clinical Orthopaedics and Related Research, vol. 466, No. 6, Jun. 1, 2008, pp. 1285-1291.

Sorenson et al., "Safety and immunogenicity of Salmonella typhimurium expressing C-terminal truncated human IL-2 in a murine model," Biologics: Targets & Therapy, vol. 4, 2010, pp. 61-73.

Soto et al., "Attenuated Salmonella typhimurium prevents the Establishment of Unresectable Hepatic Metastases and Improves Survival in a Murine Model," Journal of Pediatric Surgery, vol. 38, No. 7, 2003, pp. 1075-1079.

Soto et al., "Attenuated Salmonella typhimurium-Induced Immunity to Hepatic Colorectal Metastases," Surgery, University of Minnesota, SSO 57th Annual Cancer Symposium, Abstract P79, 2004, p. S107.

Soto et al., "Preferential Proliferation of Attenuated Salmonella typhimurium Within Neuroblastoma," Journal of Pediatric Surgery, vol. 39, No. 6, 2004, pp. 937-940.

Therasse et al., "New Guidelines to Evaluate the Response to Treatment in Solid Tumors," Journal of the National Cancer Institute, vol. 92, No. 3, Feb. 2, 2000, pp. 205-216.

Toso et al., "Phase I Study of the Intravenous Administration of Attenuated Salmonella typhimurium to Patients with Metastatic Melanoma," Journal of Clinical Oncology, vol. 20, No. 1, Jan. 2002, pp. 142-152.

Trotti et al., "CTCAE v3.0: Development of a Comprehensive Grading System for the Adverse Effects of Cancer Treatment," Seminars in Radiation Oncology, vol. 13, No. 3, Jul. 2003, pp. 176-181.

Ustun et al., "Investigation of technological properties of Nigella sativa (Black Cumin) seed oil," JAOCS, vol. 67, No. 12, Dec. 1990, pp. 958-960.

Verma et al., "Gene Therapy: Twenty First Century Medicine," Annual Review of Biochemistry, vol. 74, 2005, pp. 711-738.

Wada et al., "Antioxidant Activity and Phenolic Content of Oregon Caneberries," Journal of Agricultural and Food Chemistry, vol. 50, No. 12, Jun. 5, 2002, pp. 3495-3500.

Yang et al., "Salmonella Overcomes Drug Resistance in Tumor through P-glycoprotein Downregulation," International Journal of Medical Sciences, vol. 15, 2018, pp. 574-579.

Zhang et al., "Determination of the Optimal Route of Administration of Salmonella typhimurium A1-R to Target Breast Cancer in Nude Mice," Anticancer Research, vol. 32, pp. 2501-2508, 2012.

European Patent Office, "Extended European Search Report", Application No. 20908106.6, Dated Jan. 24, 2024, pp. 1-11.

Wasiluk et al., "QS310. Attenuated Salmonella typhimurium Expressing Human Interleukin-2 (IL-2) Invades Human Pancreatic Cancer Cells", Oncology IX: Apoptosis, Immunology, and Angiogenesis, vol. 144, Issue 2, P390, Feb. 2008, pp. 1-5.

Hiroshima et al. "Efficacy of Tumor-Targeting Salmonella typhimurium A1-R in Combination with Anti-Angiogenesis Therapy on a Pancreatic Cancer Patient-derived orthotopic xenograft (PDOX) and cellline mouse models", Oncotarget vol. 5 No. 23, Oct. 28, 2014, pp. 12346-12357.

Neoptolemos et al., "Comparison of adjuvant gemcitabine and capecitabine with gemcitabine monotherapy in patients with resected pancreatic cancer (ESPAC-4): a multicentre, open-label, randomised, phase 3 trial", Lancet vol. 389, Jan. 25, 2017, pp. 1011-1024.

Conroy et al., "FOLFIRINOX or Gemcitabine as Adjuvant Therapy for Pancreatic Cancer", The New England Journal of Medicine, vol. 379 No. 25, Dec. 20, 2018, pp. 2395-2406.

Forbes et al., "White paper on microbial anti-cancer therapy and prevention", Journal for Immunotherapy of Cancer, Biomed Central LTD, vol. 6 No. 1, Aug. 6, 2018, pp. 1-24.

Ohkawa, "The current status of FOLFIRINOX for unresectable pancreatic cancer", Journal of the Japan Pancreas Society, vol. 29, (2014), pp. 885-891, With english abstract.

* cited by examiner

200

201 — Administer first dose of attenuated *S. typhimurium* and first dose of chemotherepy agent(s)

202 — Administer second dose of attenuated *S. typhimurium*

203 — Administer second dose of chemotherapy agent(s)

204 — Administer third dose of attenuated *S. typhimurium*

205 — Administer third dose of chemotherapy agent(s)

*p<0.02

METHODS AND AGENTS FOR TREATING SOLID TUMOR CANCERS

RELATED MATTERS

This application is a US National Phase Patent Application of PCT Application No. PCT/US2020/067067, filed Dec. 26, 2020, which claims priority to U.S. Provisional Patent Application No. 62/953,792, filed Dec. 26, 2019. The entire contents of each of these applications are incorporated herein by reference.

TECHNICAL FIELD

This disclosure relates to methods and agents for treating cancer, and more particularly, to methods and agents for treating solid tumor cancers using attenuated *Salmonella typhimurium*.

BACKGROUND

Despite great progress in oncologic therapy, cancer remains the second most common cause of death worldwide. The mainstay of cancer treatment is chemotherapy with the aim of curing or controlling the cancer using the highest dose of a drug with tolerable side effects. Strategies employed to decrease the side effects include, for example, varying the combination of anti-neoplastic agents, metronomic dosing, and delivery of the chemotherapeutic agent directly to the affected organ. In the last several years, advancements have been made with immunotherapy for cancer treatment and many immunologic agents have demonstrated promise in this field. However, significant toxicities and tumor resistance limit this treatment strategy.

Due to their intrinsic immune-stimulating and cancer-targeting properties, microbial-based entities are a potential treatment for cancer. However, the results of many animal studies and limited human trials to date have been mixed. Most studies administered bacterial therapy intravenously and have been associated with significant toxicities, long after the development of metastatic disease was established, or the bacteria administered did not contain any immuno-modulatory proteins.

Thus, it would be desirable to provide a microbial-based entity for use in cancer treatment that contains such an immunomodulatory protein. It would also be desirable to provide such a treatment that is both non-toxic and effective in treating cancer.

SUMMARY

The present disclosure relates to methods and agents for treating solid tumor cancers in a subject by administering to the subject a composition consisting essentially of attenuated *S. typhimurium* with concomitant standard of care chemotherapy.

In one embodiment, the present disclosure provides a method of treating a solid tumor cancer. The method comprises administering a combination to a subject in need thereof. The combination can comprise a single chemotherapy agent or a combination of two or more chemotherapy agents, together with a dose of a composition consisting essentially of attenuated *Salmonella typhimurium*.

In another embodiment, the present disclosure provides a method of treating pancreatic cancer. The method comprises administering a combination to a subject in need thereof.

The combination can comprise a single chemotherapy agent or a combination of two or more chemotherapy agents, together with a dose of a composition consisting essentially of attenuated *Salmonella typhimurium* containing a plasmid carrying a coding sequence encoding a truncated human interleukin-2. The truncated human interleukin-2 consists of the amino acid sequence shown in SEQ ID NO: 2. In some cases, the combination of two or more chemotherapy agents comprises gemcitabine and capecitabine. In other cases, the combination of two or more chemotherapy agents comprise leucovorin, 5-fluorouracil, irinotecan, and oxaliplatin.

In yet another embodiment, the present disclosure provides a method of treating a solid tumor cancer. The method comprises administering a combination to a subject in need thereof. The combination can comprise a single chemotherapy agent or a combination of two or more chemotherapy agents, together with a dose of a composition consisting essentially of attenuated *Salmonella typhimurium* containing a plasmid carrying a coding sequence encoding a truncated human interleukin-2. The truncated human interleukin-2 consists of the amino acid sequence shown in SEQ ID NO: 2.

In another embodiment, the present disclosure provides an anti-tumor agent for use in a method of treating cancer. The anti-tumor agent comprises a combination that can comprise a single chemotherapy agent or a combination of two or more chemotherapy agents, together with a dose of a composition consisting essentially of attenuated *Salmonella typhimurium* for use in treating a solid tumor cancer. The method comprises administering the combination to a subject in need thereof.

In still another embodiment, the present disclosure provides an anti-tumor agent for use in a method of treating cancer. The anti-tumor agent comprises a combination that can comprise a single chemotherapy agent or a combination of two or more chemotherapy agents, together with a dose of a composition consisting essentially of attenuated *Salmonella typhimurium* containing a plasmid carrying a coding sequence encoding a truncated human interleukin-2. The truncated human interleukin-2 consists of the amino acid sequence shown in SEQ ID NO: 2. The method comprises administering the combination to a subject in need thereof.

DETAILED DESCRIPTION

Figure 1:
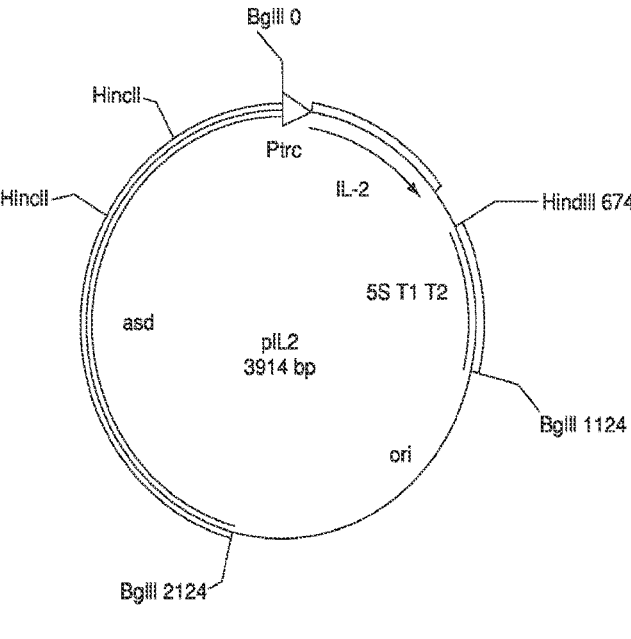
FIG. 1 shows the pIL2 plasmid containing the coding sequence encoding the human interleukin-2 protein, used to construct attenuated *S. typhimurium* with the IL-2 gene (also referred to herein as "SalpIL2").

The following detailed description is exemplary in nature and is not intended to limit the scope, applicability, or configuration of the disclosure in any way. Unless defined otherwise, all technical and scientific terms used herein have the same meaning as those commonly understood by one of ordinary skill in the art to which this invention belongs. Although methods and materials similar or equivalent to those described herein may be used in the invention or testing, suitable methods and materials are described herein. The materials, methods and examples are illustrative only, and are not intended to be limiting. Those skilled in the art will recognize that many of the noted examples have a variety of suitable alternatives. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used in the description herein and throughout the claims that follow, the meaning of "a," "an," and "the" includes plural reference unless the context clearly dictates otherwise.

"Attenuated," as used herein, means bacteria selected or altered to greatly diminish its capacity to cause disease, but still able to retain its ability to colonize the gut associated lymphoid tissue.

"Coding sequence" and "coding region," as used herein, are used interchangeably and refer to a polynucleotide that encodes a protein and, when placed under the control of appropriate regulatory sequences, expresses the encoded protein. The boundaries of a coding region are generally determined by a translation start codon at its 5' end and a translation stop codon at its 3' end.

"IL-2," as used herein, means the protein human interleukin-2.

"NK" or "NK cell," as used herein, means natural killer cell.

Due to their intrinsic immune-stimulating and cancer-targeting properties, microbial-based entities are a potential treatment for cancer. Importantly, the side effect profile from some of these microbial-based options appears far superior to cytotoxic chemotherapy and immunotherapy. However, results from animal studies and limited human trials to date have been mixed, although most studies administered bacterial therapy intravenously and have been associated with significant toxicities, long after the development of metastatic disease was established, or the bacteria administered did not contain any immunomodulatory proteins.

Attenuated *Salmonella typhimurium* has been developed as a vector to deliver therapeutic agents to tumors. The potential of *S. typhimurium* is largely due to its reported propensity to accumulate at greater than 1,000-fold higher concentration in tumors relative to healthy tissues. In addition, the genetic manipulability of *S. typhimurium* allows for the expression of foreign recombinant proteins, making these bacteria an effective delivery system for proteins that may be toxic when administered systemically.

*Salmonella typhimurium* (*S. typhimurium*) has been shown to preferentially colonize solid tumors. In particular, it infects and colonizes solid tumors and stimulates a cellular immune response after infecting cells intracellularly. As a result, it is believed to be an extremely efficient method to deliver immune modulating proteins directly to the tumor microenvironment. As one example, it has been shown that *S. typhimurium* accumulates within solid tumors at a ratio (1000:1 to 10,000:1) that is much higher than the "natural"

target organisms of *Salmonella* colonization during an infection, namely the liver and spleen.

Figure 3:
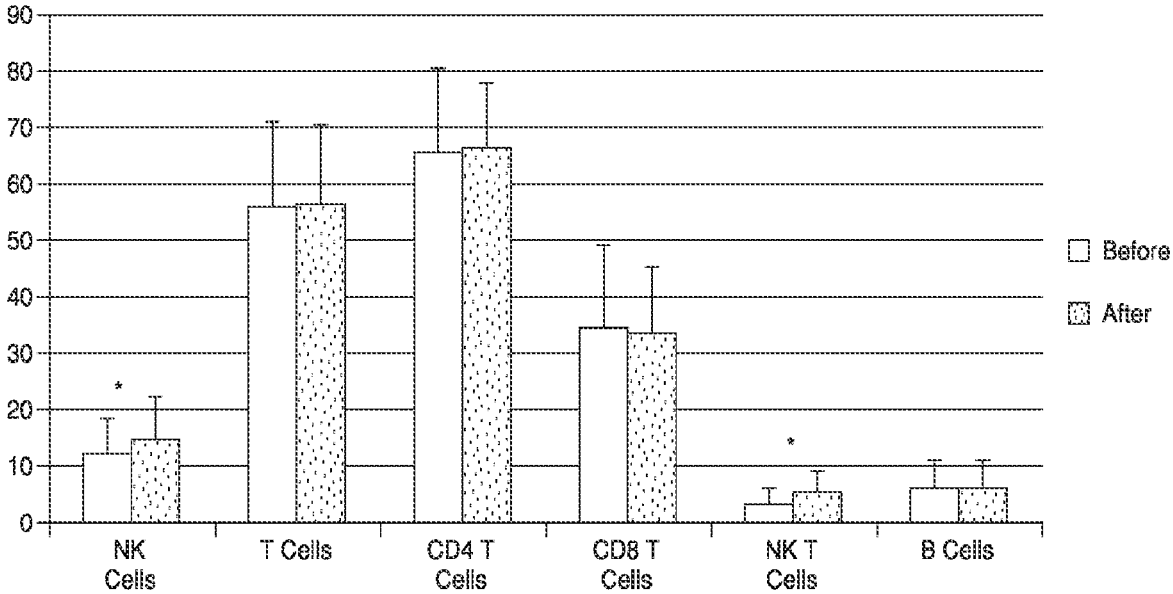
FIG. 3 is a bar graph showing effects of SalpIL2 on blood lymphocyte population five weeks after SalpIL2 has been orally administered.

Interleukin-2 (IL-2) is a protein naturally produced by the human body which promotes lymphocyte proliferation and enhances the cytolytic function of T cells and natural killer (NK) cells. It is thus able to stimulate the immune system to produce cancer-destroying white blood cells. IL-2 based immunotherapy in certain types of cancer has been studied for years with limited success. The amino acid sequence (SEQ ID NO: 3) of the normal human IL-2 protein encoded by SEQ ID NO: 4 (the DNA sequence encoding normal human IL-2) is shown in FIG. 3 of U.S. patent application Ser. No. 13/524,503, which issued as U.S. Pat. No. 8,647,618, which is a continuation of U.S. patent application Ser. No. 12/425,927, filed Apr. 17, 2009, which issued as U.S. Pat. No. 8,221,739, which is a continuation-in-part of and claims priority to U.S. patent application Ser. No. 10/834,587, filed Apr. 29, 2004, now abandoned, the contents of each of which applications are hereby incorporated by reference in their entirety.

While IL-2 is naturally produced by the human body, its maximum effectiveness requires a higher concentration and more specific delivery vector to the disease site. However, high doses of IL-2 are found to result in severe toxicity in many patients. A solution to this problem is using a live bacterial strain of *Salmonella typhimurium* which was attenuated to greatly diminish its capacity to cause disease. *S. typhimurium* is used due to its natural ability to colonize the gut associated lymphoid tissue (GALT), liver and spleen. Colonization of the liver by the attenuated *S. typhimurium* further initiates a generalized cellular response against the bacteria or can persist as a carrier state. The χ4550 strain of *S. typhimurium* used in the present disclosure contains a gene deletion constructed by transposon mutagenesis with Tn10 followed by selection for furasic acid resistance. This method of genetic alteration leads to deletional loss of Tn10 and adjacent DNA sequences to produce a deletion of aspartate semialdehyde dehydrogenase (asd). This mutation imposes a requirement for diaminopimelic acid. The lack of the asd enzyme in these bacteria leads to the inability to construct a stable cell wall causing lethal lysis of the *S. typhimurium*. Thus, to ensure stable expression of a desired protein, a plasmid (pYA292) was constructed which carries the asd gene.

FIG. 1 shows the pIL2 plasmid containing the coding sequence encoding the human interleukin-2 protein, used to construct SalpIL2, attenuated *S. typhimurium* with the IL-2 gene. In order to ensure avirulence of the *S. typhimurium* strain, standard P22 phage transduction of the mouse virulent *S. typhimurium* SR-11 strain χ3306 was employed to construct the χ4550 strain that lacks the ability to synthesize adenylate cyclase and the cAMP receptor protein (CRP). Cyclic AMP and cAMP receptor protein are necessary for the transcription of many genes and operons concerned with the transport and breakdown of catabolites. Although cAMP is found in mammalian tissue and theoretically could be used by the bacteria to increase the potential for virulence, the lack of a cAMP receptor protein should abolish any benefit that could occur by the uptake of cAMP by these mutant bacteria.

A synthetic cDNA (SEQ ID NO: 5), coding for a truncated human IL-2 protein, optimized for expression in *Escherichia coli* was inserted into plasmid pYA292 using well-known methods. The truncated cDNA (SEQ ID NO: 1) is a part of the synthetic IL-2 nucleotide sequence (SEQ ID NO: 5). This sequence is one nucleotide short of the sequence that was intended to code for a full-length mature human IL-2 protein. As used herein, "mature" means a protein lacking the beginning (N-terminal) 20 amino acid signal sequence that is cleaved off as the molecule is secreted from a human cell. The mutation that occurred is a deletion of a "t" nucleotide between the "a" at position 272 and the "g" at position 273. This resulted in an in-frame taa stop codon at position 274 that truncated the resultant IL-2 protein. The resulting DNA nucleotide sequence is SEQ ID NO: 1 and the expressed protein is SEQ ID NO: 2.

Both the aspartate semialdehyde dehydrogenase (asd+) vector and the synthetic truncated human IL-2 cDNA were digested to completion with restriction enzymes EcoRI (Promega® Corporation, Madison, Wis.) and HindIII (New England Biolabs® Corporation, Beverly, Mass.). The about ~3.4 kb linearized vector fragment of pYA292 and the EcoRI-HindIII fragment of the IL-2 gene were isolated following agarose gel electrophoresis using the PrepaGene Kit (BioRad, Hercules, Calif.). The IL-2 gene fragment was ligated into the pYA292 vector using T4 DNA ligase (Promega® Corporation, Madison, Wis.) with a 3:1 molar excess of insert and incubating for 4 hours at 16° C. The ligation mix was then electroporated into the χ4550 strain of attenuated *S. typhimurium*. *S. typhimurium*, Δcya-1 Δcrp-1 ΔasdA1 strain χ4550 was grown in Luria Broth (Sigma® Corporation, St. Louis, Mo.) containing 50 mg/ml diaminopimelic acid (DAP).

Cultures were grown to an absorbance of 0.200 at OD600 (approximately $10^8$ colony forming units (cfu)/ml broth) and the cells were prepared for electroporation. Plasmid vector pYA292 and the ligation mix were electroporated into χ4550 utilizing an electroporation device (BioRad) with 0.2 cm disposable cuvettes. Cells were pulsed at 2.5 kV and 25 μF with a pulse controller at 200 ohms. Cells were then subsequently plated on Luria agar without DAP and recombinant clones were identified using the Magic Mini-Prep DNA Purification System (Promega® Corporation), and restriction enzyme digestion with EcoRI and HindIII and gel electrophoresis with 1.2 agarose. The restriction enzyme mapping revealed a plasmid corresponding to that expected for an insert of the IL-2 fragment in pYA292 and the plasmid was renamed pIL2. The new transformant was renamed χ4550 (pIL2), also referred to herein as "SalpIL2."

Transforming an asd deleted strain with the plasmid (pIL2) allows for the stable expression of IL-2. As discussed above, stability of this vector is maintained because the particular strain of *S. typhimurium* used here (χ4550) lacks the enzyme aspartate semialdehyde dehydrogenase (asd), which, conversely, the plasmid containing the IL-2 gene (pIL2) contains. Bacteria lacking asd cannot make diaminopimelic acid (DAP), an essential component of the bacterial cell wall and, thus, would not long survive. Thus, if the attenuated *S. typhimurium* were to attempt to revert to its wild-type strain and lose the plasmid, it would die a "DAP-less" death. Because the loss of the IL-2 containing plasmid would also result in the loss of the plasmid encoded asd, stable expression of the IL-2 gene is achieved.

Figure 2:
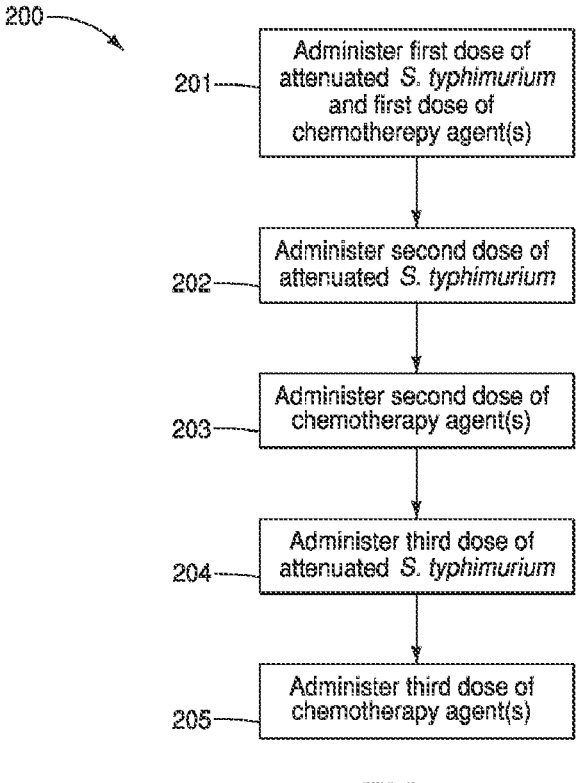
FIG. 2 is a flow diagram of a method of treating cancer with a combination of attenuated *S. typhimurium* and at least two chemotherapy agents according to various embodiments.

FIG. 2 is a flow diagram of method 200. Method 200 relates to a method of treating cancer with a combination of attenuated *S. typhimurium* and a single chemotherapy agent or a combination of two or more chemotherapy agents according to various embodiments. The cancer being treated in method 200 can be any solid tumor cancer, including, but not limited to, liver cancer, lung cancer, pancreatic cancer, breast cancer, prostate cancer, skin cancer, kidney cancer, bone cancer, gastrointestinal cancers, cancers of the soft tissue (e.g., muscle cancer), adrenal cancer, colon cancer, and bladder cancer. In certain exemplary embodiments, the cancer being treated is pancreatic cancer. In any embodiment of the present disclosure, the cancer being treated can be a metastatic or non-metastatic cancer and can optionally be a refractory cancer.

Method 200 includes administering a combination treatment to a subject in need thereof. The combination treatment can include a step 201 of administering a first dose of attenuated *S. typhimurium* and a first dose of a single chemotherapy agent (or a combination of two or more chemotherapy agents) to the subject. In some embodiments, the subject is a mammal. In any embodiment of the present disclosure, the mammal can be a human.

The method 200 can involve administering a single dose of the combination to the subject (i.e., administering only the first dose of attenuated *S. typhimurium* and a first dose of a single chemotherapy agent, or a combination of two or more chemotherapy agents, to the subject). Alternatively, the method 200 can involve administering multiple doses to the same subject over a certain period of time (e.g., over a period of weeks, such as every two weeks, every three weeks, every four weeks, etc.). For example, the method 200 can include any one or more of the following steps: administering a second dose of attenuated *S. typhimurium* (202); administering a second dose of a single chemotherapy agent or a combination of two or more chemotherapy agents (203); administering a third dose of attenuated *S. typhimurium* (204); and administering a third dose of a single chemotherapy agent or a combination of two or more chemotherapy agents (205). The steps of administering a second dose of attenuated *S. typhimurium* (202) and administering a second dose of a single chemotherapy agent or a combination of two or more chemotherapy agents (203) can occur on the same day, or such treatment can be staggered (such that these steps occur on different days). Similarly, the steps of administering a third dose of attenuated *S. typhimurium* (204), and administering a third dose of a single chemotherapy agent or a combination of two or more chemotherapy agents (205) can occur on the same day, or such treatment can be staggered (such that these steps occur on different days).

As discussed above, method 200 need not include all the steps shown in FIG. 2. For example, in some embodiments, method 200 may exclude the steps of administering a second dose of attenuated *S. typhimurium* (202) and administering a third dose of attenuated *S. typhimurium* (204). Additionally, method 200 can include additional steps, such as administering a fourth dose of attenuated *S. typhimurium* and/or administering a fourth dose of a single chemotherapy agent or a combination of two or more chemotherapy agents. In addition or alternatively, method 200 may exclude the steps of administering a second dose of a single chemotherapy agent or a combination of two or more chemotherapy agents (203); and may exclude the steps of administering a third dose of a single chemotherapy agent or a combination of two or more chemotherapy agents (205).

The number of doses of both the attenuated *S. typhimurium* and the single chemotherapy agent (or combination of two or more chemotherapy agents) in method 200 can be varied depending on the particular patient, the type of cancer being treated, and the patient's response to previous doses.

Each dose of attenuated *Salmonella typhimurium* can be part of a composition consisting essentially of attenuated *Salmonella typhimurium*. In some such cases, the dose of attenuated *Salmonella typhimurium* contains a plasmid carrying a coding sequence encoding a truncated human interleukin-2, wherein the truncated human interleukin-2 consists of the amino acid sequence shown in SEQ ID NO: 2. Thus, in such cases, the attenuated strain of *Salmonella typhimurium* has been engineered to carry the human gene for IL-2 to impart an immunologically mediated tumor cell kill within the tumor microenvironment.

In some embodiments, the dose of attenuated *Salmonella typhimurium* administered (during steps of method 200) can be from $10^3$ to $10^{12}$ colony forming units (e.g., from $10^6$ to $10^{11}$ colony forming units, or from $10^5$ to $10^{10}$ colony forming units). However, such dosages are not required in all embodiments, and alternative *S. typhimurium* dosages are also contemplated.

In certain embodiments, administering each dose of the attenuated *S. typhimurium* can include orally administering the attenuated *S. typhimurium*. By administering *Salmonella*-IL2 orally, systemic toxicity related to the gram-negative bacteria itself can be avoided. In one embodiment, administering a dose of attenuated *S. typhimurium* includes administering an oral dose of SalpIL2 of from $10^5$ to $10^{10}$ colony forming units.

In certain embodiments, the single chemotherapy agent or combination of two or more chemotherapy agents are administered intravenously or orally. However, skilled artisans will appreciate that any suitable administration route can be used to administer the chemotherapy agent(s) of method 200.

In some embodiments, administering a dose of a single chemotherapy agent or a combination of two or more chemotherapy agents includes administering gemcitabine and capecitabine. In other embodiments, administering a dose of a single chemotherapy agent or a combination of two or more chemotherapy agents includes administering two or more of (and in some cases, each of) leucovorin, 5-fluorouracil, irinotecan, and oxaliplatin. The combination of each of leucovorin, 5-fluorouracil, irinotecan, and oxaliplatin is commonly referred to as "FOLFIRINOX." In other embodiments, the at least two chemotherapy agents can comprise two or more chemotherapy agents not specifically recited herein.

Method 200 is advantageous, because the combination allows a lower and less toxic dose of the chemotherapy agent(s) to be used. This provides effective treatment while minimizing side effects caused by toxicity of the chemotherapy agents.

Certain embodiments of the present disclosure provide an anti-tumor agent for use in a method of treating cancer. In some cases, the anti-tumor agent can be used in method 200 discussed above.

EXAMPLES

Safety Study

This study was a dose escalation study to determine the safety of administering SalpIL2. Patients with histologically confirmed solid tumors metastatic to the liver and no effective therapy available were enrolled in the study.

Immediately prior to administration, each patient was given 30 mL of orally administered Maalox® antacid or Mylanta® antacid to neutralize gastric acid. A single dose of orally administered SalpIL2 was then given. The dose was prepared by diluting a thawed glycerol stock in 30 mL saline. Immediately after administration of the dose of SalpIL2, each patient was given 200 mL saline orally, and then took nothing orally for at least one hour.

The planned dose escalation began with $10^5$ colony forming units of bacteria with an increase by one order of magnitude until a maximum dose of $10^{10}$ colony forming unit, while monitoring for dose limiting toxicity (DLT).

Description and grading scales for adverse event reporting were adopted from the revised National Cancer Institute Common Toxicity Criteria (CTC) version 3.0 guidelines. DLT was defined as sepsis syndrome, grade 4 vomiting or diarrhea, or other grade 3 toxicities. Close follow-up was planned for 11 weeks post administration with enrollment of one to two patients per month.

Patients with measurable disease were assessed for response and progression using the Response Evaluation Criteria in Solid Tumors (RECIST) Committee criteria. In addition to adverse event monitoring, flow cytometry was conducted on peripheral blood samples to look at immune cell sub-populations to determine the immunologic effect from the study biological drug.

Results and Conclusion

In total, 22 patients were enrolled and administered SalpIL2. Eight patients did not complete the trial, as shown in Table 1 below. No adverse events were judged to be likely or definitely due to study enrollment. All blood and stool cultures were negative for the study organism.

TABLE 1

| Enrollment and Study Completion | | | |
|---|---|---|---|
| Dose (Bacteria Administered) | Patients | Patients enrolled at 5 weeks | Reason for failing to complete the study |
| $10^5$ | 1-6 | 6 | |
| $10^6$ | 7-9 | 2 | Patient 9 died. |
| $10^7$ | 10-12 | 2 | Patient 11 died. |
| $10^8$ | 13-15 | 1 | Patient 14 removed from study due to disease progression. Patient 15 died. |
| $10^9$ | 16-18 | 1 | Patient 16 hospitalized at local hospital. Patient 17 died. |
| $10^{10}$ | 19-22 | 2 | Patients 19 and 22 died. |

Overall, there was no statistically significant difference between serum chemistries and complete blood counts tested at the pre-study visit compared with 5 weeks after administration (N=14). Comparing the low dose ($10^5$) versus the high dose ($10^{10}$) cohorts, there was a slight difference in the mean change in platelet count between pre-study and 5 weeks after administration (+58,500+/−86,720 versus −40,667+/−356,978/mL, p=0.046), but there were no other statistically significant differences in the laboratory values tested.

FIG. 3 is a bar graph showing a comparison of samples taken pre-administration with samples drawn 5 weeks post oral administration for all doses administered. As illustrated in FIG. 3, post-administration samples demonstrated a statistically significant increase in the percent peripheral blood NK cells (mean=12.1 vs 14.6%, p=0.02) and NK T cells (mean=3.4 vs 5.6%, p=0.02), but no statistically significant difference in the other cell populations measured. The number of patients with 5-week post administration samples for each dose arm was six ($10^5$ CFU), 2 ($10^6$ CFU), 2 ($10^7$ CFU), 1 ($10^8$ CFU), 1 ($10^9$ CFU), and 2 ($10^{10}$ CFU).

Subsequently to demonstrating the absence of toxicity and an immunologic response to a single oral dose of *Salmonella*-IL2 in this Phase I study, approval from Health Canada was granted for a n=1 trial for a multiple dose trial of *Salmonella*-IL2 with adjuvant chemotherapy for a patient with Stage 4, metastatic pancreas cancer (referred to below ad throughout this disclosure as "Patient 1"). SalpIL2 was administered to Patient 1 every two weeks with standard of care chemotherapy. Now, 11 months following diagnosis, Patient 1 has not experienced any toxicity to SalpIL2 and continues her therapy, has normalized her carbohydrate antigen (CA) 19-9 values, demonstrated a strong NK response with fluorescence-activating cell sorting (FACS) analysis, and demonstrated a radiologic regression of metastatic tumor burden.

The results of this Phase I dose escalation study show that oral attenuated S. *Typhimurium* containing the human IL-2 gene (SalpIL2) demonstrated an immunologic response and caused no significant toxicities up to doses of $10^{10}$ CFU. Previous studies utilizing attenuated *Salmonella* or other bacteria have not been as promising as this one. A trial utilizing VNP20009 with patients with metastatic melanoma did not demonstrate survival efficacy and revealed toxicity with intravenously administered bacteria. Similarly, a recent report of a Phase IIb study in patients with metastatic pancreas cancer that were randomized to receive chemotherapy or a *Listeria* vaccine did not demonstrate a survival difference.

Case Study

A patient with metastatic pancreas cancer (hereinafter referred to as "Patient 1") individually sought out the possibility of receiving SalpIL2 in addition to her standard of care chemotherapy.

Patient 1 was a 70 year old female with a past medical history of hypercholesterolemia and presented with a several week history of abdominal pain and bloating. Patient 1's workup eventually elucidated a 3.9×5.7 cm mass in the tail of the pancreas with invasion of the splenic hilum and left adrenal gland. In addition, there were multiple metastatic nodules in the lungs and liver of Patient 1. Subsequent fine needle aspiration and biopsy confirmed the diagnosis of Stage 4 pancreatic ductal adenocarcinoma. Patient 1 was immediately started on the FOLFIRINOX regimen of leucovorin, 5-fluorouracil, irinotecan, and oxaliplatin administered every two weeks. Well aware of her prognosis of a median survival of 11.1 months, Patient 1 reached out for the possibility of adding SalpIL2 to her treatment regimen. Thus, five months after starting the chemotherapeutic regimen, and after receiving approval for a n=1 Investigational New Drug Application from Health Canada and approval from the Research Ethics Board (REB) of the Jewish General Hospital and the Faculty of Medicine Research of McGill University in Montreal, Quebec, Canada, Patient 1 started a regimen of oral SalpIL2 given concomitantly every two weeks for six doses. If a response was noted, the treating oncologist could opt for continued administration of SalpIL2 every two weeks indefinitely. To evaluate Patient 1's response and to monitor for potential toxicity, scheduled visits with her oncologist included the following: CA19-9 evaluation, complete blood count, comprehensive metabolic panel, periodic MRI of chest and abdomen, and blood drawn for flow cytometric analysis sent to MD Biosciences, Oakdale, MN.

Figure 4:
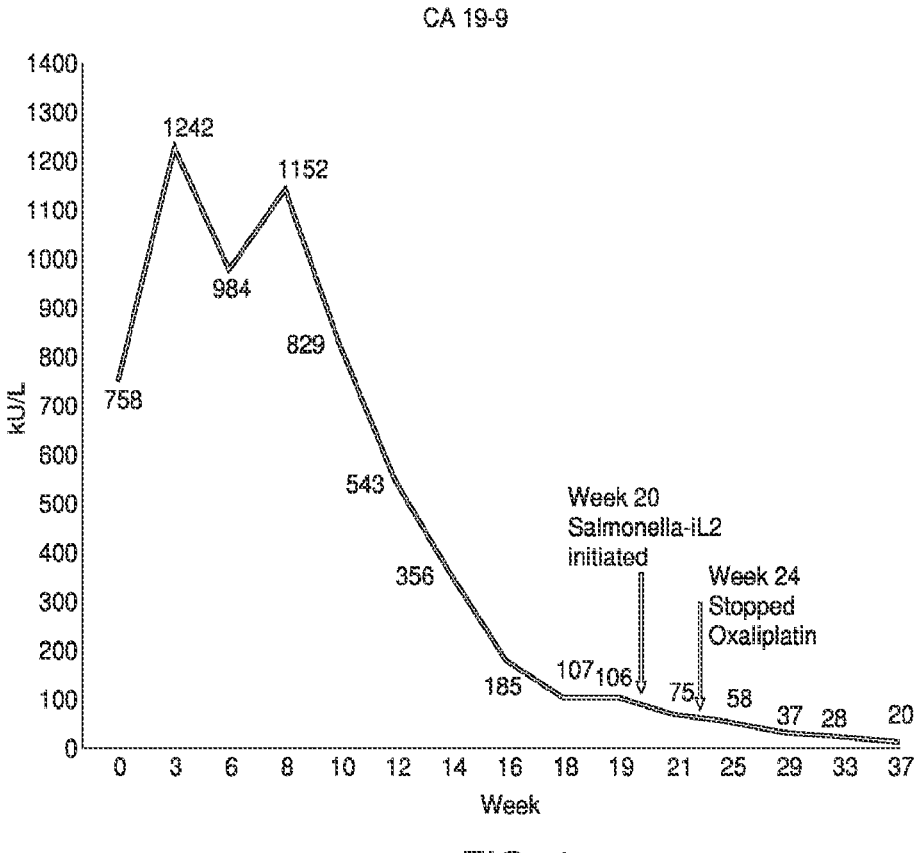
FIG. 4 is a line graph showing CA 19-9 levels versus weeks of treatment for Patient 1.
Figure 5:
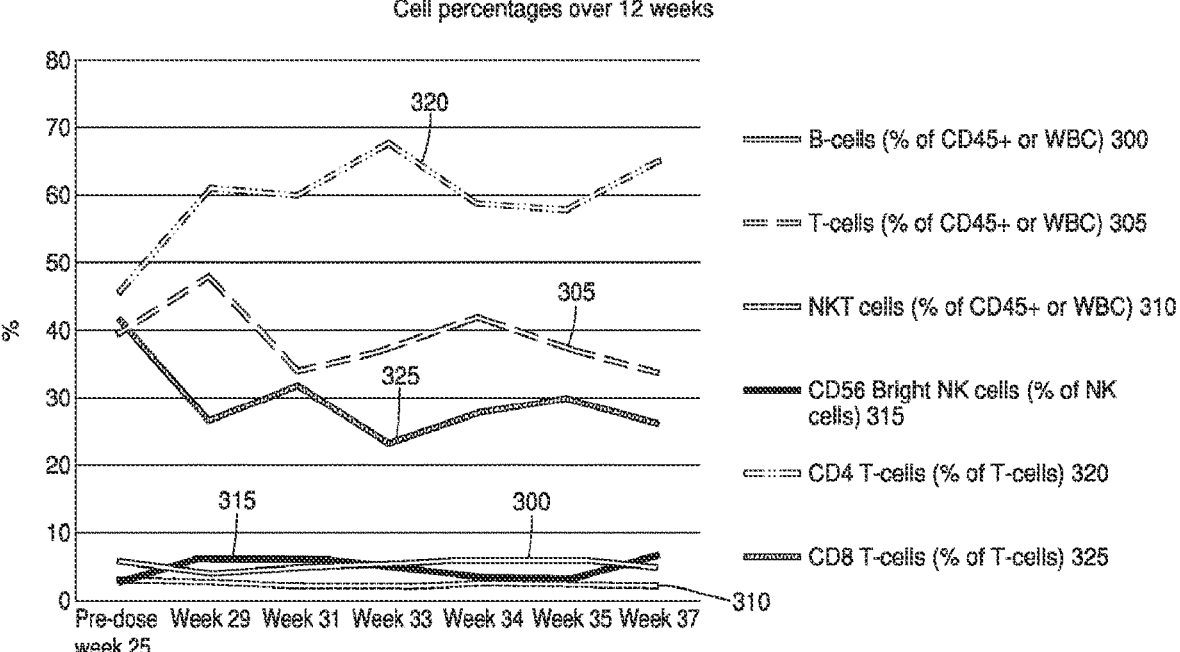
FIG. 5 is a line graph showing various cell percentages versus weeks of treatment for Patient 1.
Figure 6:
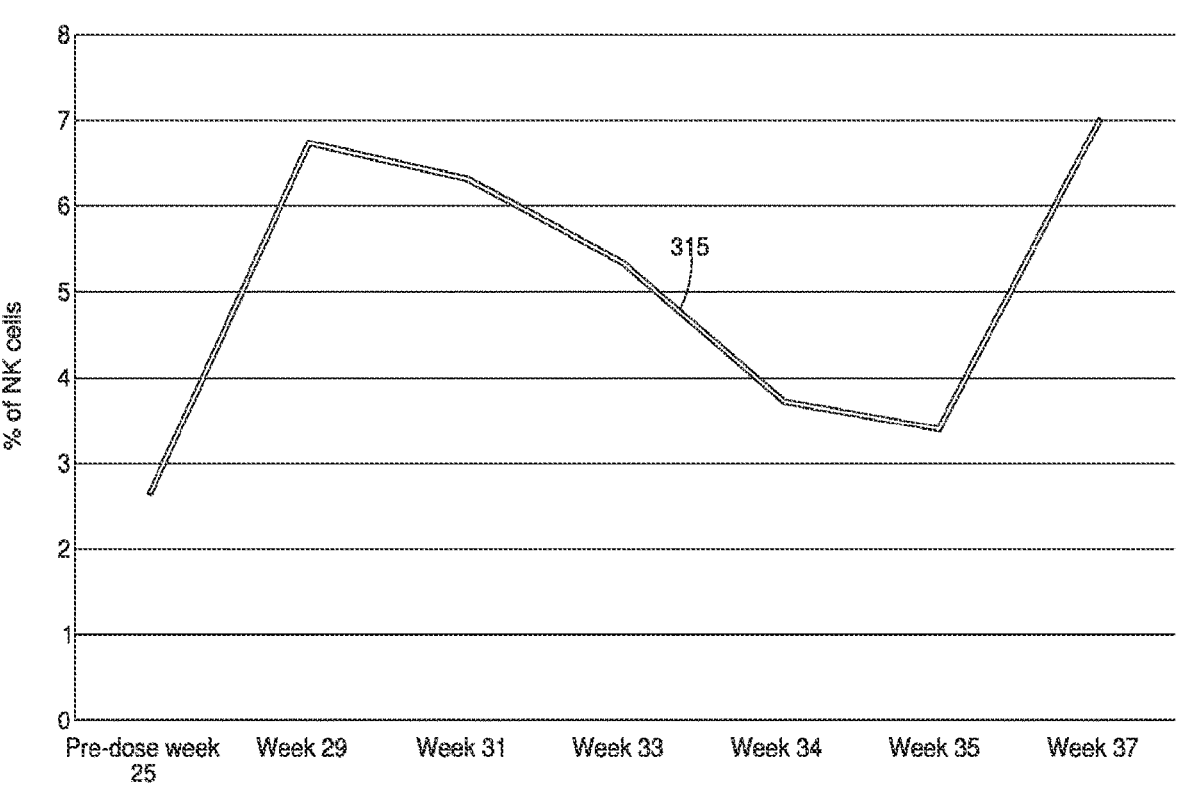
FIG. 6 is a line graph showing percent of CD56 Bright NK cells versus weeks of treatment for Patient 1.
Figure 7:
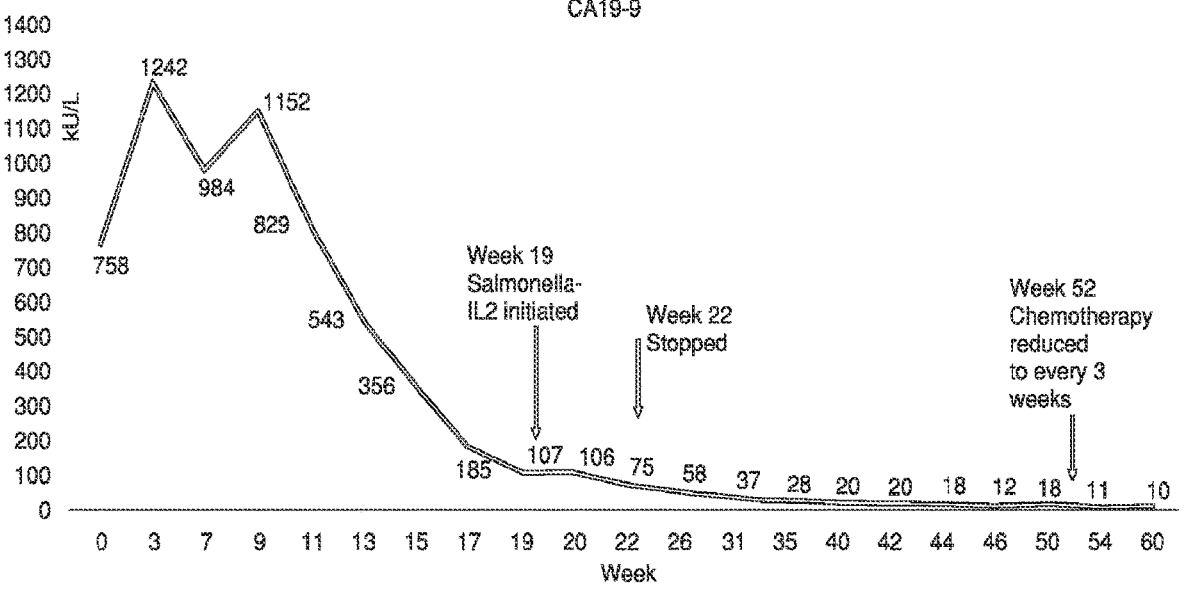
FIG. 7 is yet another line graph showing CA 19-9 levels in Patient 1 from 0 to 15 months (based on time from initial diagnosis with metastatic pancreas cancer).

Upon diagnosis, Patient 1's CA19-9 level was markedly elevated and there was a positive response to FOLFIRINOX over five months with a plateauing of the CA19-9 level to 75-100 kU/L for one month (see FIGS. 4 and 7). In addition, by month six, Patient 1 began to experience severe neurotoxicity from oxaliplatin as manifested by absence of feeling in both her hands and feet. Thus, administration of oxaliplatin to Patient 1 was stopped. At month five, SalpIL2 was added to Patient 1's treatment regimen and by the sixth month, her CA19-9 levels normalized and have stayed in the normal range for the past eleven months. Furthermore, periodic magnetic resonance imaging revealed overall reduction in size of the primary pancreatic mass from 5.4×3.4 cm to 4.9×2.2 cm. In addition, there were interval decreases in the size of the hepatic metastases from an average of 1.7 cm in greatest dimension to 1.1 cm. The MRI also revealed that there were no new metastatic lesions in the liver or anywhere else and the signal intensity of these metastatic deposits was appreciably much less than when the patient initially presented. Lastly, flow cytometric analysis of peripheral blood performed every two weeks prior to administration of systemic chemotherapy has demonstrated a significant increase in the CD56$^{bright}$ NK cells (315) when compared to baseline (FIGS. 5 and 6). CD4 T cells (320) also have demonstrated a significant increase. However, as also shown in FIG. 5, despite the cytotoxic chemotherapy, there has been no decrease in Patient 1's other major cell populations, including B cells (300), T cells (305), NKT cells 310, and CD8 T cells (325). Additionally, although there was no PET scan obtained at diagnosis, a scan obtained at month 14 did not demonstrate any metabolic activity in the metastatic tumor deposits (i.e., showing a complete absence of tumor activity by PET scan).

Patient 1 has not reported any adverse effects from the SalpIL2. Namely the patient has not had any fevers, diarrhea, nausea, or vomiting. To date, all stool cultures of the patient taken every two weeks have been negative for *Salmonella*, including stool cultures obtained after an episode of diarrhea at approximately week 48.

Typically, treatment of metastatic pancreatic cancer with FOLFIRINOX demonstrates a therapeutic response for approximately six to eight months and then the majority of patients experience a significant progression of their disease with median survival of 11.1 months. In this case, despite eliminating oxaloplatin because of the neurotoxic side effects, now at month 15, the patient continues to feel well and is vigorously participating in activities of daily living. Furthermore, given this response seen in her CA19-9 levels and radiologic response, it was decided to continue SalpIL2 indefinitely.

Results and Discussion

The results of a Phase I dose escalation study show that a single oral dose of SalpIL2 caused no significant toxicities up to doses of $10^{10}$ colony forming units. The most commonly reported adverse events included pain in the abdomen or sides, weakness, and loose stools. Some patients experienced self-limiting diarrhea. However, no *Salmonella* was cultured in the stool of any of the patients. Peripheral blood chemistries and CBC with white cell differential showed no significant differences between the pre and post administration time periods. The cause of a slight difference in platelet count changes between the low and high dose cohorts is not readily apparent. Although no patients had a clinical response during the study period, all patients already had significant metastatic disease prior to enrollment.

The flow cytometric analysis of peripheral blood showed a statistically significant increase in the percentage circulating NK cells and NK T cells when comparing the pre-study period to five weeks post administration. These finding were not dose-dependent and were consistent with previous preclinical studies that showed an increase in systemic NK cell activation after administration of oral SalpIL2, which may account for the effect of this therapy in decreasing the rate of metastatic osteosarcoma to the lung in a dog (an organ not typically associated with S. *typhimurium* infiltration).

In addition, the portion of the present disclosure relating to this case study outlines the first use of SalpIL2 in a multiple dosing strategy in a patient (Patient 1) with metastatic pancreas cancer. Pre-clinical studies demonstrated synergism between SalpIL2 and doxorubicin and various mechanisms for this synergism have been suggested. Patient 1 demonstrated a significant increase in CD56$^{bright}$ NK cells, which have been shown to be one of the major subsets infiltrating some cancers and, upon cytokine stimulation of this cell line, can undergo a significant differentiation into a highly cytotoxic NK cell.

Despite having to stop a component of the chemotherapeutic strategy, namely oxaloplatin, Patient 1 is demonstrating a major response clinically and radiologically. In addition, flow cytometry revealed that despite cytotoxic chemotherapy, immunologic cell populations were maintained. With these encouraging results, an expanded multiple dose Phase II trial of *Salmonella*-IL2 of up to 60 patients with metastatic pancreas cancer will be initiated.

When various cancer cell lines were studied in vitro, it was discovered that *Salmonella*-IL2 invaded hepatocytes most readily when compared with hepatoma, neuroblastoma, adenocarcinoma, and osteosarcoma. However, when examining the division efficiency (i.e., the ability to divide in a tumor once colonization occurred), osteosarcoma and neuroblastoma had the highest division efficiency.

Furthermore, in vivo experimentation has demonstrated that orally administered *Salmonella*-IL2 can robustly colonize a variety of tumor types. Because *Salmonella* can colonize solid tumors, Applicant believes that *Salmonella*-IL2 can act as a "smart bomb" by invading and locally releasing IL-2 into the tumor microenvironment, while avoiding any systemic toxicity from the IL-2.

While some preferred embodiments of the present disclosure have been described, it should be understood that various changes, adaptations, and modifications may be made therein without departing from the spirit of the invention and the scope of the appended claims.

| SEQUENCES |
|---|
| DNA sequence for truncated interleukin-2 (homo sapiens) (SEQ ID NO: 1) |

| | | | | | |
|---|---|---|---|---|---|
| ATGGCTCCTA | CTAGCTCGAG | CACTAAGAAA | ACTCAACTGC | AATTGGAGCA | TCTGCTGCTG | 60 |
| GATCTGCAGA | TGATTCTGAA | TGGCATCAAT | AACTACAAGA | ACCCTAAGCT | GACTCGCATG | 120 |
| CTGACTTTCA | AATTCTACAT | GCCGAAAAAG | GCTACCGAGC | TCAAACATCT | CCAGTGCCTG | 180 |
| GAAGAGGAAC | TGAAGCCGCT | GGAGGAAGTA | CTTAACCTGG | CACAGTCTAA | GAACTTCCAC | 240 |
| CTGCGTCCGC | GTGACCTGAT | CTCCAACATC | AAGTAA | | | 276 |

| Protein sequence for truncated interleukin-2 (homo sapiens) (SEQ ID NO: 2) |
|---|

```
Met Ala Pro Thr Ser Ser Ser Thr Lys Lys Thr Gln Leu Gln Leu Glu
1               5               10                          15

His Leu Leu Leu Asp Leu Gln Met Ile Leu Asn Gly Ile Asn Asn Tyr
            20              25              30

Lys Asn Pro Lys Leu Thr Arg Met Leu Thr Phe Lys Phe Tyr Met Pro
        35              40              45

Lys Lys Ala Thr Glu Leu Lys His Leu Gln Cys Leu Glu Glu Glu Leu
    50              55              60

Lys Pro Leu Glu Glu Val Leu Asn Leu Ala Gln Ser Lys Asn Phe His
65              70              75              80

Leu Arg Pro Arg Asp Leu Ile Ser Asn Ile Lys
            85              90
```

The invention claimed is:

1. An anti-tumor agent for use in a method of treating cancer, the anti-tumor agent comprising a combination comprising at least two chemotherapy agents selected from gemcitabine, capecitabine, leucovorin, 5-fluorouracil, irinotecan, and oxaliplatin; and a composition consisting essentially of attenuated *Salmonella typhimurium* containing a plasmid carrying a coding sequence encoding a human interleukin-2, wherein the human interleukin-2 consists of the amino acid sequence shown in SEQ ID NO: 2.

2. The anti-tumor agent of claim 1, wherein the cancer is selected from liver cancer, lung cancer, pancreatic cancer, breast cancer, prostate cancer, skin cancer, kidney cancer, bone cancer, gastrointestinal cancers, cancers of the soft tissue, muscle cancer, adrenal cancer, colon cancer, and bladder cancer.

3. The anti-tumor agent of claim 1, wherein the anti-tumor agent comprises about $10^5$ to $10^{10}$ colony forming units/ml of broth of the attenuated *Salmonella typhimurium*.

* * * * *

SEQUENCE LISTING

<160> NUMBER OF SEQ ID NOS: 2

<210> SEQ ID NO 1
<211> LENGTH: 276
<212> TYPE: DNA
<213> ORGANISM: Homo sapiens

<400> SEQUENCE: 1
atggctccta ctagctcgag cactaagaaa actcaactgc aattggagca tctgctgctg     60
gatctgcaga tgattctgaa tggcatcaat aactacaaga accctaagct gactcgcatg    120
ctgactttca aattctacat gccgaaaaag gctaccgagc tcaaacatct ccagtgcctg    180

-continued

```
gaagaggaac tgaagccgct ggaggaagta cttaacctgg cacagtctaa gaacttccac        240
ctgcgtccgc gtgacctgat ctccaacatc aagtaa                                   276

<210> SEQ ID NO 2
<211> LENGTH: 91
<212> TYPE: PRT
<213> ORGANISM: Homo sapiens

<400> SEQUENCE: 2

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Lys
                85                  90
```